United States Patent
Knobel (10) Patent No.: US 10,458,997 B2
(45) Date of Patent: Oct. 29, 2019

(54) SIGNAL OFFSET DETERMINATION AND CORRECTION

(71) Applicant: Roche Diagnostics Operations, Inc., Indianapolis, IN (US)

(72) Inventor: Rolf Knobel, Rotkreuz (CH)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 203 days.

(21) Appl. No.: 15/690,430

(22) Filed: Aug. 30, 2017

(65) Prior Publication Data

US 2018/0067140 A1 Mar. 8, 2018

(30) Foreign Application Priority Data

Sep. 5, 2016 (EP) .................................... 16187217

(51) Int. Cl.
*G01N 21/01* (2006.01)
*G01N 21/27* (2006.01)
(Continued)

(52) U.S. Cl.
CPC .......... *G01N 35/00693* (2013.01); *G01J 3/28* (2013.01); *G01N 21/03* (2013.01);
(Continued)

(58) Field of Classification Search
CPC ......... G01J 3/28; G01N 21/03; G01N 21/253; G01N 21/272; G01N 21/274; G01N 21/82;
(Continued)

(56) References Cited

U.S. PATENT DOCUMENTS

| | | |
|---|---|---|
| 4,150,295 A | 4/1979 | Wieder |
| 5,291,426 A | 3/1994 | Collins et al. |

(Continued)

FOREIGN PATENT DOCUMENTS

| | | |
|---|---|---|
| EP | 0049561 A1 | 4/1982 |
| EP | 1059522 A1 | 12/2000 |

(Continued)

OTHER PUBLICATIONS

Gujral, P. et al., Measurement-Based Drift Correction in Spectroscopic Calibration Models, https://infoscience.epfl.ch/record/126335/files/4CAC, 2008, 5 pp., retrieved Mar. 9, 2017.

*Primary Examiner* — Maureen Wallenhorst
(74) *Attorney, Agent, or Firm* — Roche Diagnostics Operations, Inc.

(57) ABSTRACT

A method for determining a background shift is presented. The method includes obtaining a plurality of optical measurement sets of a sample taken by a sample analyzer at different points in time. Each set includes one measurement taken in a first channel and another measurement taken in a second channel different from the first channel. The plurality of optical measurement sets includes one set group and another set group. The measurements in the one set group show a higher signal change than the measurements in the other group. A first background signal is determined based on a relation of measurements in the first and second channels in the one group. A second background signal is determined based on a relation of measurements in the first and second channels in the one group and the other group. A background shift is determined based on the first and second background signals.

11 Claims, 6 Drawing Sheets

(51) Int. Cl.
*G01N 35/00* (2006.01)
*G01N 21/82* (2006.01)
*G01N 21/25* (2006.01)
*G01J 3/28* (2006.01)
*G01N 21/03* (2006.01)

(52) U.S. Cl.
CPC ......... *G01N 21/253* (2013.01); *G01N 21/272* (2013.01); *G01N 21/274* (2013.01); *G01N 21/82* (2013.01); *G01N 35/00* (2013.01); *G01N 2201/127* (2013.01)

(58) Field of Classification Search
CPC .. G01N 21/63; G01N 21/64; G01N 2201/127; G01N 35/00; G01N 35/00693
USPC ............. 436/43, 164, 172; 422/82.05, 82.08, 422/82.09
See application file for complete search history.

(56) References Cited

U.S. PATENT DOCUMENTS

| | | | |
|---|---|---|---|
| 6,635,886 B1 | 10/2003 | Rushbrooke et al. | |
| 8,571,811 B1 | 10/2013 | Mueller | |
| 2013/0084592 A1* | 4/2013 | Seiple | G01N 21/274 435/29 |
| 2015/0044780 A1* | 2/2015 | Kurz | G01N 21/274 436/501 |
| 2015/0099309 A1* | 4/2015 | Krufka | G01J 1/44 250/216 |
| 2017/0176478 A1* | 6/2017 | Harbers | G01N 21/274 |

FOREIGN PATENT DOCUMENTS

| | | |
|---|---|---|
| WO | 1997/010494 A1 | 3/1997 |
| WO | 2014/064447 A1 | 5/2014 |

* cited by examiner

SIGNAL OFFSET DETERMINATION AND CORRECTION

CROSS-REFERENCE TO RELATED APPLICATIONS

This application is a continuation of EP 16187217.1, filed Sep. 5, 2016, which is hereby incorporated by reference.

BACKGROUND

The present disclosure relates to methods for determining a background shift in an optical measurement signal and an analyzer comprising a background shift detection module.

Optical measurement methods of different kinds are employed in a plurality of automated sample analyzers. For instance, clinical chemistry analyzers can be configured to measure the absorbance of biological samples to determine single or multiple parameters of the biological samples based on this measurement. The optical measurements can be subject to different types of background signals. One technique to reduce the influence of background signals is the bi-chromatic correction technique. This technique can involve taking measurements at two different wavelengths and subtracting these two measurements to remove a constant background signal contained in both measurement signals. However, in some situations the background signal might vary over time, e.g., after a cuvette movement. This can render bi-chromatic correction techniques and other correction techniques less reliable and/or precise.

SUMMARY

According to the present disclosure, a method for determining a background shift comprised in optical measurement signals of an analyzer for samples is presented. The method can comprise obtaining a plurality of sets of optical measurements of a sample taken by the analyzer for samples at different points in time. Each set can include at least one measurement taken in a first channel ($l_1$) and another measurement taken in a second channel ($l_2$) different from the first channel. The plurality of sets of optical measurements can include one group of sets (group A) and another group of sets (group B). The measurements in the one group of sets (group A) can be taken during a different period of time than the measurements in the other group of sets (group B). The measurements in the one group of sets (group A) can show a higher signal change than the measurements in the other group (group B). The method can also comprise determining a first background signal (bA) based on a relation of measurements in the first and second channels ($l_1$, $l_2$) in the one group (A), determining a second background signal (bB) based on a relation of measurements in the first and second channels in the one group (A) and the other group (B), and determining a background shift based on the first and second background signals (bA, bB).

In accordance with one embodiment of the present disclosure, an automated sample analyzer is presented. The automated sample analyzer can comprise an optical measurement device configured to determine one or more parameters of a sample. The optical measurement device can be configured to measure the parameter at least at a first channel and a second channel different from the first channel. The automated sample analyzer can also comprise a background shift detection module configured to prompt the analyzer to carry out the operations of the above method.

Other features of the embodiments of the present disclosure will be apparent in light of the description of the disclosure embodied herein.

BRIEF DESCRIPTION OF THE SEVERAL VIEWS OF THE DRAWINGS

The following detailed description of specific embodiments of the present disclosure can be best understood when read in conjunction with the following drawings, where like structure is indicated with like reference numerals and in which.

DETAILED DESCRIPTION

In the following detailed description of the embodiments, reference is made to the accompanying drawings that form a part hereof, and in which are shown by way of illustration, and not by way of limitation, specific embodiments in which the disclosure may be practiced. It is to be understood that other embodiments may be utilized and that logical, mechanical and electrical changes may be made without departing from the spirit and scope of the present disclosure.

A method for determining a background shift comprised in optical measurement signals of an analyzer for samples is presented. The method can include obtaining a plurality of sets of optical measurements of a sample taken by the analyzer for samples at different points in time. Each set can include at least one measurement taken in a first channel and another measurement taken in a second channel different from the first channel. The plurality of sets of optical measurements can include one group of sets and another group of sets. The measurements in the one group of sets can be taken during a different period of time than the measurements in the other group of sets and the measurements in the one group of sets can show a higher signal change than the measurements in the other group. The method can also include determining a first background signal based on a relation of measurements in the first and second channels in the one group, determining a second background signal based on a relation of measurements in the first and second channels in the one group and the other group, and determining a background shift based on the first and second background signals.

An automated sample analyzer is presented that can include an optical measurement device configured to determine one or more parameters of an optical sample. The optical measurement device can be configured to measure the parameter at least in a first channel and a second channel different from the first channel. The automated sample analyzer can also include a background shift detection module configured to make the analyzer obtain results of a plurality of sets of optical measurements of a sample taken by the analyzer for samples at different points in time. Each set can include at least one measurement taken in the first channel and another measurement taken in the second channel. The plurality of sets of optical measurements can include one group of sets and another group of sets. The measurements in the one group of sets can be taken during a different period of time than the measurements in the other group of sets and the measurements in the one group of sets can show a higher signal change than the measurements in the other group. A first background signal can be determined based on a relation of measurements in the first and second channels in the one group. A second background signal can be determined based on a relation of measurements in the first and second channels in the one group and the other group. A background shift can be determined based on the first and second background signals.

The above method and the above apparatus can have one or more of the following advantages in some embodiments. Firstly, the techniques of the present disclosure can allow for detecting that a background shift happened at a predetermined point in time in some examples. For instance, the background shift can be wavelength dependent which can mean the background shift may have different values in the first and second channel.

For instance, a vessel containing a sample can be slightly turned or displaced by an analyzer in the process of adding a reagent into the vessel. In this situation, a tilt of the surface of the vessel relative to the light path of the measurement device can be changed. As a result, measurements taken before and after this event can have different background signals. In this example, the background shift can also exhibit a wavelength dependency.

In another example, a vessel containing a sample may be scratched or contaminated during a manipulation of the vessel by the analyzer. This may also introduce a varying background signal (both in time and in wavelength). The techniques of the present invention can allow detection if such types of background shifts have happened. As a result, imprecise or even faulty measurement results can be avoided in some examples.

Secondly, the background signal detection process can happen automatically and during run-time in some examples. This can allow for selecting an appropriate measure to deal with an event causing the varying background signal early enough to limit the adverse consequences of such event. For example, in some prior known analyzers costly repetitions of measurements may be required if an error due to a varying background signal is detected after the fact (which may not be possible on the same sample in some assays on biological samples after a certain time has passed). Avoiding such situations or reducing the frequency of occurrence of such situations can make the measurement process more reliable and/or more resource-efficient.

Thirdly, the techniques of the present disclosure can allow for correcting background shift in some examples. This can happen automatically in some examples. In this manner, the idle time of an automated analyzer can be reduced as measurements can be carried out (with a relatively high precision) even though a certain background signal variation is present. In other examples, the requirements regarding precision of the sample handling processes may be relaxed when employing the techniques of the present disclosure as a certain level of background signal variation can be corrected and thus tolerated. This can make the analyzer hardware less complex and thus cheaper in some examples.

After having provided an overview over the techniques of the present disclosure, in the following paragraphs several terms will be discussed which are used in the present disclosure in a particular manner.

The term 'light' as used in the present disclosure can include, but is not limited to, radiation in the wavelength range visible for humans. As used in the present disclosure, light can also include radiation in the non-visible part of the spectrum (e.g., in the UV or infrared part of the spectrum). In some examples, light can include radiation having a wavelength of over 200 nm and below 10,000 nm (for instance, a wavelength between 350 nm and 1000 nm).

The expression 'optical measurement' can include any measurement on a sample in which light (including infrared or UV radiation) emitted by the sample can be collected. In one example, an optical measurement can include guiding light towards a sample and measuring light emanating from the sample in response. This emanating light can be linearly scattered light. For instance, an optical measurement can include reflectance, transmittance or absorbance measurements.

In other examples, an optical measurement can include detecting inelastically scattered light. For instance, the luminance of a sample (e.g., the fluorescence) can be detected in some examples of optical measurements. Even though some examples discussed below are related to reflectance, transmittance or absorbance measurements, the techniques described herein can also be applied in analyzers using other optical measurement techniques.

The expression 'measurement at a wavelength' may not be limited to a measurement in a relatively narrow spectral band (or at a single wavelength in an idealized case). Rather, the expression 'measurement at a wavelength' can refer to a measurement collecting radiation having a particular spectral distribution (all spectral distributions discussed herein can be characterized by a full width half maximum bandwidth unless stated otherwise). In some examples, this particular spectral distribution can be a fairly narrow distribution (e.g., narrower than 10 nm full width half maximum bandwidth). In some examples, the measurement bandwidth can be 2 nm or less (e.g., if an illumination light source is a CW laser or another light source having a narrow bandwidth).

However, in other examples, the spectral distribution of the radiation collected in a measurement can range over a broader spectral range. In some examples, the measurement range can have a bandwidth of 30 nm or more (or 50 nm or more). In some examples, radiation emitted by a light emitting diode and scattered or inelastically reflected by a sample can be detected to obtain a 'measurement at a wavelength.' Even in these "broad bandwidth" cases the comparatively broad wavelength band can be characterized by a single wavelength (e.g., a center wavelength of the wavelength band).

The term 'measurement a wavelength' can refer to a wavelength of the radiation collected from the sample. The illumination light and also the light emitted by the sample may include additional or other spectral components. For example, emission or re-emitted light can be filtered by optical filters to take a measurement at a specific wavelength.

The expression 'measurement at a different wavelength' can include a situation in which the wavelength bands of two sources of different wavelength (for 'taking measurement at different wavelengths') partially (though not completely) overlap. For instance, a first measurement may be taken at a wavelength between 500 nm and 550 nm and a second measurement at a wavelength between 545 nm and 600 nm. These two wavelengths can still be considered to be 'different' as defined in the present disclosure.

In one illustrative example, an illumination light source can include multiple different light emitting diodes (e.g., a red, a green and a blue light emitting diode). A 'red' light emitting diode may emit light having a wavelength between 600 nm and 630 nm, a 'green' light emitting diode may emit light between 515 and 550 nm, and a 'blue' light emitting diode may emit light between 400 nm and 420 nm. In this situation, transmitted light of the red light emitting diode can be light of a different wavelength than the transmitted light of the green and blue light emitting diodes.

The terms 'analyzer'/'analytical work cell'/'analytical unit' as used herein can encompass any apparatus, or apparatus component, that can measure analytical properties of a sample, e.g., following a reaction of a sample with a reagent for obtaining a measurement value.

An analyzer can be operable to determine one or more parameters of a sample or a component thereof. For example, a parameter can be an absorption, transmittance or reflectance of the sample contained in a cuvette. In other examples, a parameter can be a fluorescence of a sample after having been illuminated with excitation light. Apart from the optical measurement devices of an analyzer discussed below (e.g., to determine an absorption, transmittance or reflectance), an analyzer can include measurement devices to determine a parameter of the sample via one or more chemical, biological, physical, or other technical procedures.

An analyzer may be operable to determine the parameter of the sample or of at least one analyte, process the determined parameter and return an obtained measurement value. The list of possible analysis results returned by the analyzer can comprise, without limitation, concentrations of the analyte in the sample, a qualitative (yes or no) result indicating the existence of the analyte in the sample (corresponding to a concentration above the detection level), optical parameters, DNA or RNA sequences, data obtained from mass spectroscopy of proteins or metabolites and physical or chemical parameters of various types.

An analytical work cell may comprise units for pipetting, dosing, and mixing of samples and/or reagents. The analyzer may comprise a reagent holding unit for holding reagents to perform the assays. Reagents may be arranged for example in the form of containers or cassettes containing individual reagents or group of reagents, placed in appropriate receptacles or positions within a storage compartment or conveyor. It may comprise a consumable feeding unit. The analyzer may comprise a process and detection system whose workflow is optimized for certain types of analysis. Examples of such analyzers can be clinical chemistry analyzers, coagulation analyzers, immunochemistry analyzers, urine analyzers, hematology analyzers, nucleic acid analyzers, used to detect the result of chemical or biological reactions or to monitor the progress of chemical or biological reactions.

The term 'sample' can refer to material(s) that may potentially contain an analyte of interest. The sample can be derived from a biological source, such as a physiological fluid, including blood, saliva, ocular lens fluid, cerebrospinal fluid, sweat, urine, stool, semen, milk, ascites fluid, mucous, synovial fluid, peritoneal fluid, amniotic fluid, tissue, cultured cells, or the like. The biological sample can be pretreated prior to use, such as preparing plasma from blood. Methods of treatment can involve centrifugation, filtration, distillation, dilution, concentration and/or separation of sample components including analytes of interest, inactivation of interfering components, and the addition of reagents. A biological sample may be used directly as obtained from the source or used following a pretreatment to modify the character of the sample. In some embodiments, an initially solid or semi-solid biological material can be rendered liquid by dissolving or suspending it with a suitable liquid medium. In some examples, the sample can be suspected to contain a certain antigen or nucleic acid.

Particular aspects of the methods for determining a background shift in an optical measurement signal and an analyzer including a background shift detection module will be discussed subsequently.

In connection with FIG. 1 to FIG. 3, some aspects of the determination and correction of a background shift in an optical measurement signal will be discussed. Subsequently, in connection with FIG. 4 to FIG. 6, different aspects of analyzers including a background shift detection module according to the present disclosure will be treated in more detail.

Figure 1:
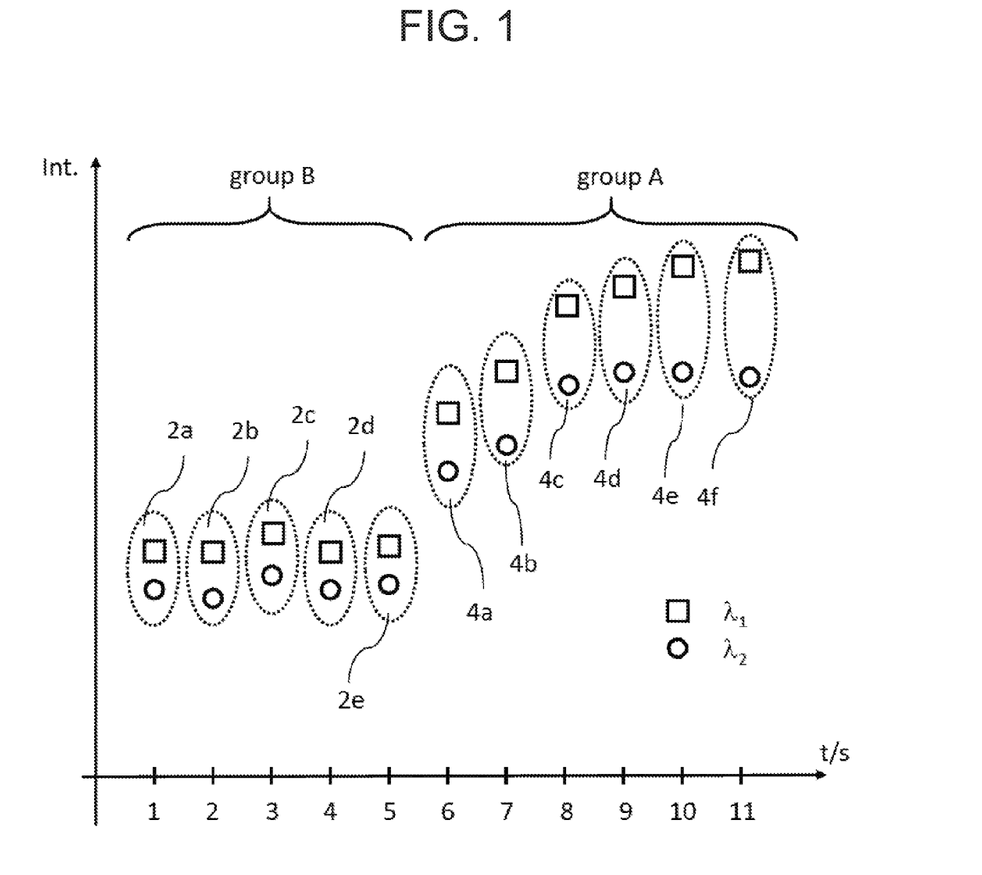
FIGS. 1-3 illustrate an example method for determining a background shift in an optical measurement signal according to an embodiment of the present disclosure.
Figure 2:
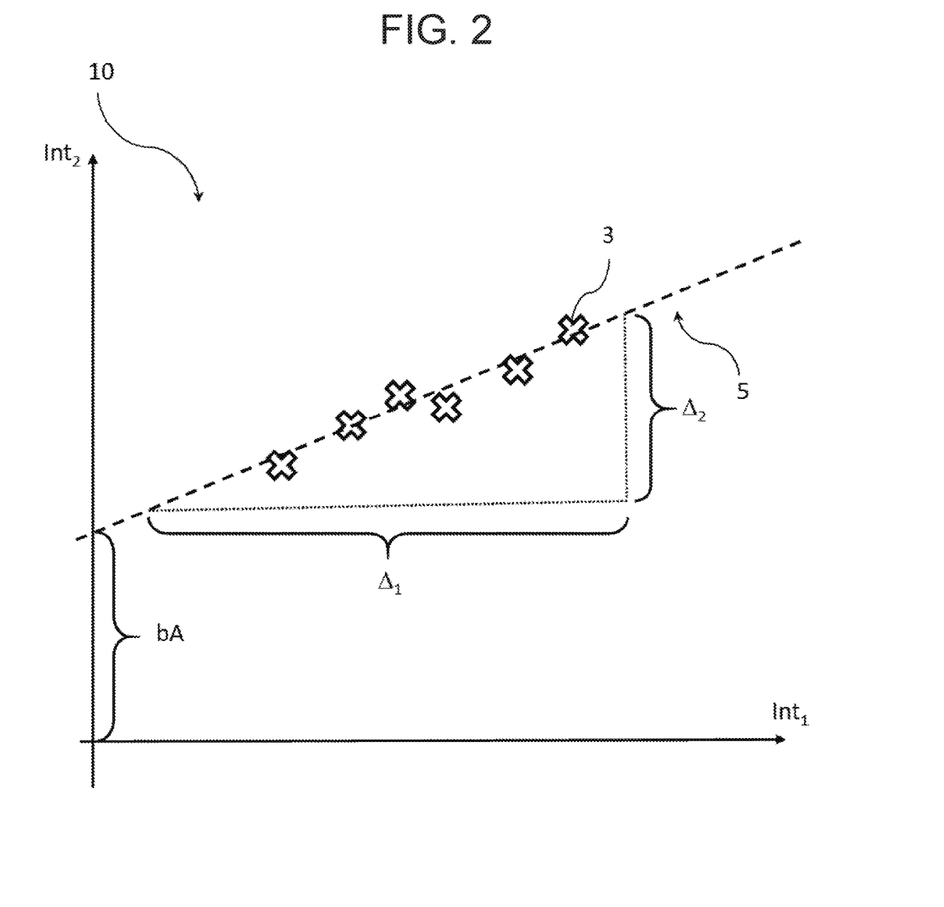
Figure 3:
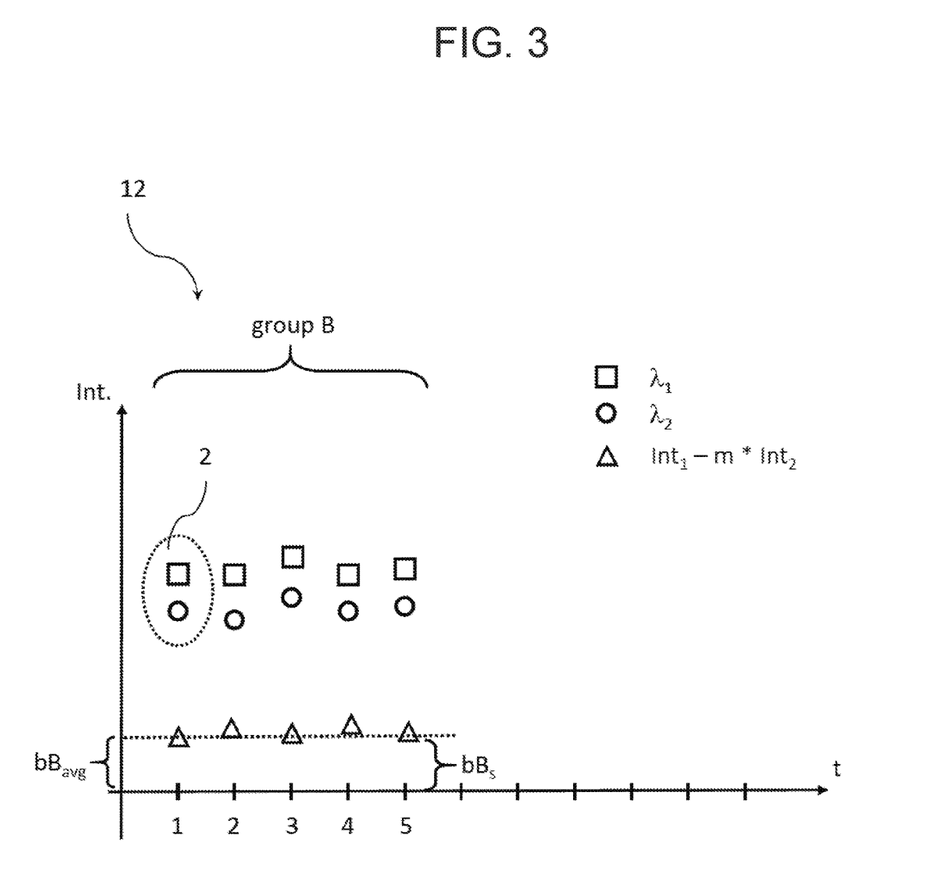

FIG. 1 to FIG. 3 illustrate a method for determining a background shift in an optical measurement signal of an analyzer for samples. The method can include obtaining results of a plurality of sets of optical measurements 2a-2e, 4a-4f of a sample taken by the analyzer for samples at different points in time, each set 2a-2e, 4a-4f including at least one measurement taken in a first channel (e.g., a measurement taken at a first wavelength $\lambda_1$) and another measurement taken in a second channel different from the first channel (e.g., taken at a second wavelength $\lambda_2$ different from the first wavelength $\lambda_1$), the plurality of sets 2a-2e, 4a-4f of optical measurements including one group of sets ("group A") and another group of sets ("group B"), the measurements in the one group of sets ("group A") being taken during a different period of time than the measurements in the other group of sets ("group B") and the measurements in the one group of sets ("group A") showing a higher signal change than the measurements in the other group ("group B").

The method of FIG. 1 to FIG. 3 can further include determining a first background signal based on a relation of measurements in the first and second channels 4a-4f in the one group ("group A"), determining a second background signal based on a relation of measurements in the first and second channels 2a-2e, 4a-4f in the one group (A) and the other group (B), and determining a background shift based on the first and second background signals.

Subsequently, the one group ("group A") can also be referred to as 'second group' and the other group ("group B") can also be referred to as 'first group'. Even though the measurements of the first group can be taken before the measurements of the second group in the example of FIG. 1, these attributes may not imply a temporal order. Rather, the one group ("group B") or second group ("group A") can be the group showing a higher signal change. In some examples, the group with the higher signal change (i.e., the one group or second group) may also be a group of measurements taken earlier in time than the other group or first group. In the same manner, the measurements in the first and second channel can also be labelled as 'first' and 'second' measurements. These attributes may not imply any temporal order.

Different aspects and features of the different steps of the method for determining a background shift will subsequently be discussed in more detail. It is understood that a method according to the present disclosure can include one or more of the below discussed aspects alone or in combination.

As can be seen in FIG. 1, the sets of optical measurements 2a-2e, 4a-4f can be separated into the two groups (in the example of FIG. 1 between time t=5 s and t=6 s). In general, the analyzer can split the sets of measurements in the first and second groups of sets of measurements ("group A" and "group B") as part of the background shift determination procedure. This splitting of the sets of measurements 2a-2e, 4a-4f can happen in several different ways.

In a first example, the splitting point can be determined based on identifying an event happening between two sets of measurements. For instance, the event can be an adding of a reagent to a sample container (e.g., a cuvette). This adding of the reagent can initiate a reaction in the sample container which can change the optical properties of the sample and, in turn, can lead to a non-stationary signal change (e.g., as can be seen in group A as shown in FIG. 1). In one example, an automated sample manipulator (e.g., a pipettor) can add the reagent to a sample vessel.

In other examples, the predefined event can be another interaction of a sample container manipulator (e.g., a cuvette gripper) of an automated analyzer with a sample container including the sample. For example, an automated sample manipulator (e.g., a pipettor) can remove material from a sample vessel. In still other examples, a container including the sample may be moved or transported between the measurements of the different sets. For instance, a sample vessel may be removed from a first position to a second position in an analyzer (e.g., a position in which a reagent can be added or an incubation position) and subsequently moved back to the first position or a different measurement position. These and other types of actions can introduce a background shift as described herein.

In other examples, the predefined event can be an action carried out by the automated analyzer (e.g., a movement of a movable part of the analyzer, e.g., opening or closing of a door of the analyzer). In still other examples, the predefined event can be a change in the ambient conditions of the analyzer (e.g., as detected by a sensor included in the analyzer or connected to the analyzer) or an adaptation of the measurement device performing the optical measurements.

The occurrence of the above described events can be detected by the analyzer, e.g., based on sampling respective sensors. In other examples, the occurrence of the events can be detected by monitoring a control queue of the analyzer. For instance, an analyzer can detect that a reagent is to be introduced into a vessel by identifying a respective instruction in a control queue of the analyzer.

In a second example, a point in time forming the boundary between the first and second groups ("group A" and "group B") can be determined based on a change in one or more characteristic of the measurement data.

For example, a moving average of the measurements in the first and/or second channels may change at some point in time (e.g., by exceeding a predefined threshold value). In other examples, a difference between subsequent measurements in the first and/or second channels may change at some point in time (e.g., by exceeding a predefined threshold value). In still other examples, a value of a standard deviation of measurements in the first and/or second channels (or other parameter characterizing a dispersion of the measurements) may change at some point in time. In these examples, the boundary between the sets of measurements of the first and second groups ("group A" and "group B") can be determined by analyzing the measurement data itself. In some examples, changes in the measurement data may be indicative of an occurrence of one of the events discussed in the preceding section.

In the preceding examples, the boundary between the sets of measurements of the first and second groups ("group B" and "group A") can be determined based on a direct or indirect determination of a trigger event. All the trigger events can have in common that they may mark a point in time at which a background shift may occur. This point in time can be determined to mark the boundary between the sets of measurements belonging to the first and second group ("group A" and "group B") and thus split the sets of measurements into the first and second groups.

In some examples, the analyzers of the present disclosure can continuously monitor the measurement data for an occurrence of events which can mark a point in time at which a background shift might occur. Whenever a background shift may have occurred, the analyzers of the present disclosure can perform the background shift detection (and potentially also correction) techniques described in the present disclosure.

A monitoring window for the sets of measurements can be arbitrarily selected. In one example, the monitoring window can be selected so that at least two sets of measurements can be contained in each of the first and second group (e.g., at least four sets of measurements or at least ten sets of measurements). The number of sets of measurements may not have to be equal in both groups. In the example of FIG. 1, the second group ("group A") can include six sets of measurements 4a-4f while the first group ("group B") can include five sets of measurements 2a-2e. A larger number of measurements in the first and second groups may enhance a precision of the background shift determination and correction processes in some examples.

In other examples, the background shift determination (and possibly correction) procedure can happen separately from the data acquisition process in the analyzer. For example, the analyzer may in a first step acquire the measurement data described in the present disclosure and transmit the measurement data for storage in a storage device. In a subsequent data processing phase, the measurement data can then be processed using the techniques of the present disclosure. In other words, the determination (and correction) techniques described herein can also be performed ex-post (e.g., to enhance a precision of a result).

As described above, the techniques of the present disclosure can include determining which group of measurements has a higher signal change. This step will be discussed in more detail in the following sections.

As can be seen in FIG. 1, a signal change in the second group ("group A") can be larger than a signal change in the first group ("group B").

In the example of FIG. 1, the measurement signals in the first group ("group B") can be substantially stationary (i.e., the measurement values can only vary due to random noise present in the respective measurement environment). The measurement signals in the second group ("group A"), on the other hand, can be non-stationary (i.e., the measurement values can vary due to a systematic temporal change of the samples optical properties). In other words, the measurement signals in the first group ("group B") can be substantially stable while the measurement signals in the second group ("group A") can change in time.

For example, a reagent may have been added to the sample and a reaction can be ongoing while the measurements in the second group ("group A") can be taken. In this example, an absorption of the sample at the two wavelengths $\lambda_1$ and $\lambda_2$ may continuously rise (or fall) while the reaction is ongoing. As a result, the measurements of the second group ("group A") can show a rising signal level in both channels. The measurements of the first group ("group B"), on the other hand, can have relatively stable signal levels as the sample may be in a relatively stationary state before the reagent is added.

Even though the example of FIG. 1 shows a negligible signal change for the first group ("group B"), this may not have to be the case for all situations in which the techniques of the present disclosure is applied. In some examples, both groups of measurements can exhibit a temporal signal change. For instance, the earlier group of measurements may be taken after a first reagent has been added to the sample. Then, a second reagent may be added and the measurements of the second group may be taken.

The determination of the magnitude of a signal change can happen in one of the following ways.

In one example, a maximum spread of the measurements in the first and second groups in the first or second channels can be compared (e.g., a larger spread of the measurements in the first or second channels). In another example, an average of the spreads of the measurements in the first and second channels can be calculated and compared. In still other examples, another measure for an amount of variation or dispersion of the measurements in the first and second groups ("group A" and "group B") can be employed (e.g., a standard variation or a higher order variation). Outliers may be identified and excluded in some examples.

Coming back to FIG. 1, it can be seen in FIG. 1 that each set of measurements $2a$-$2e$, $4a$-$4f$ can include one measurement taken at the first wavelength $\lambda_1$ and one measurement taken at the second wavelength $\lambda_2$. In the example of FIG. 1, both measurements of each set can be taken at substantially the same time. However, in other examples, there can be a predetermined temporal distance between two measurements at the first and second sets of measurements (e.g., smaller than 30% of a temporal distance between two subsequent measurements at the same wavelength).

In addition, the example of FIG. 1 (and all subsequent examples) can use intensity as a measurement value determined in the optical measurements. However, the techniques described herein may not be limited to measured intensities. Rather, any suitable measurement value can be used in the techniques described herein. For instance, the measurement may include absorbance, transmittance or reflectance measurements in other examples.

After the sets of measurements have been split into first and second groups and the one of the groups having a larger signal change has been selected, the measurements in the first and second groups can be processed to determine a background shift. An example process will be subsequently discussed in connection with FIG. 2 and FIG. 3.

The measurements in the first and second channels of the second group ("group A") having the larger signal change can be processed in a first step. A relation between the measurements in the first and second channels of the second group ("group A") can be determined.

In one example, as can be seen in FIG. 2, this can involve determining a linear correlation 10 between the measurements in the first and second channels (e.g., at first and second wavelengths). In FIG. 2, each data point 3 in the depicted graph can stand for one set of measurements $4a$-$4f$ in the second group ("group A") as shown in FIG. 1 (please note that FIG. 2 is a schematic illustration and may not be a true representation of the values as shown in FIG. 1). The intensity (or any other measurement value) of the measurements at the second wavelength $Int_2$ can be shown on the abscissa while the intensity (or any other measurement value) at the first wavelength $Int_1$ can be shown on the ordinate. Accordingly, FIG. 2 illustrates a degree of correlation of the measurements at the first and second wavelengths. In other examples, the correlation can be calculated the other way around (the subsequent steps may have to be changed accordingly).

As can be seen in FIG. 2, the degree of linear correlation can be relatively high in the example. Based on a correlation function, a first axis intercept bA and a slope m of the correlation function can be determined. These two parameters can be used for determining a background drift in an optical measurement signal. In other examples, any other suitable proportionality factor other than slope m can be used.

In the example of FIG. 2, the measurement signals can exhibit a comparatively strong linear correlation. This can mean that the correlation function can define a line 5 extending close to the data points 3 encoding the intensities of the measurements at the two wavelengths in the second group ("group A"). In one example, the analyzer can determine the first axis intercept bA and the slope m of the correlation function by using a linear regression technique or any other technique to determine a degree of linear correlation between two sets of samples. In this example, the slope m can indicate the amount by which a signal level of the second channel changes $\Delta_2$ when the signal level of the second channel can change by a given amount $\Delta_1$. The first axis intercept bA can be the intensity hypothetically measured in the second channel when the intensity at the first wavelength $Int_1$ is zero. A linear correlation between the measurements in the first and second channels may be found in situations where a spacing between the first and second channels can be relatively narrow (e.g., less than 50 nm).

However, in other examples, the correlation between the measurements in the first and second channels (e.g., at first and second wavelengths) may be non-linear. In these cases, an analyzer can still determine a correlation parameter and a first axis intercept. For example, the analyzer may determine a non-linear correlation function (e.g., by a non-linear regression technique). Based on this non-linear correlation function, a first axis intercept and a slope (which can be a function of the measurement signal level in some examples) can be determined.

Moreover, even though FIG. 2 shows a positive correlation between the measurements in the first and second channel, the correlation may also be negative in other examples. The techniques of the present disclosure can equally be applied in these situations.

After the first axis intercept bA and a slope m have been determined, the process can continue with processing the measurements in the first group ("group B") as shown in FIG. 3.

In a first operation, the measurements in the first group in the second channel (e.g., taken at the second wavelength $\lambda_2$) and the measurements in the first group taken in the first channel (e.g., at the first wavelength $\lambda_1$) can be compared by using the relation determined based on the measurements in the second group ("group A") in the preceding step (e.g., the correlation between the measurements in the second group).

In one example, this can involve using the slope m which can determine a relation between the signal levels in the first and second channels. For instance, the measurements in the first group taken in the first channel (e.g., at the second wavelength $\lambda_1$) can be multiplied by the slope and subtracted from measurements in the first group taken in the second channel (e.g., at the first wavelength $\lambda_2$). This can yield a second axis intercept. As shown in FIG. 2, the second axis intercept can be calculated as:

$$bB = Int_2 - m^* Int_1 \qquad \text{(equation 1)}.$$

In addition, in some examples, determining the second axis intercept can include averaging over multiple sets of measurements 2 in the first group ("group B"). For example, the measurements in the first channel can be averaged and the measurement in the second channel can be averaged. Then, the second axis intercept $bB_{avg}$ can be calculated based on the averaged values for the measurements in the first and second channels. In other examples, each set can be first processed by using the slope m and the resulting differences can be averaged in a further step to obtain the second axis intercept $bB_{avg}$.

In other examples, a single set of measurements in the first group ("group B") can be processed to determine the second axis intercept $bB_S$. For example, the second axis intercept $bB_S$ can be determined by using equation 1 above only for the first set of measurements 2.

However, a larger number of sets used for calculating the second axis intercept may improve the precision of the estimation and correction process in some examples. In particular, in some examples, the variations in background shifts determined by using the techniques of the present disclosure can be fairly small so that averaging the measurements in the first group ("group B") can be desirable.

Regardless of the exact technique employed to determine the first and second axis intercepts dA and dB, the first and second axis intercepts dA and dB can be used to determine if a background shift has taken place between the measurements of the first or second groups or not (e.g., caused by one of the events discussed above). The first and second axis intercepts dA and dB can thus be examples of first and second background signals as described herein. This operation will be discussed in more detail in the subsequent passages.

In one example, the first and second axis intercepts bB, bA can be compared to estimate if a background shift may have taken place between the measurements of the first and second groups.

For instance, it can be determined if the first and second axis intercepts bB, bA deviate by more than a predetermined threshold. The predetermined threshold can be an absolute threshold or it can be a relative threshold depending on the signal level of the measurements. If the first and second axis intercepts bB, bA do not differ by more than the predetermined threshold, it can be assumed that no background shift has taken place between the measurements of the first and second groups. Accordingly, if the first and second axis intercepts bB, bA do differ by more than the predetermined threshold, it can be assumed that a background shift has taken place between the measurements of the first and second groups In one example, it can be determined if the first and second axis intercepts bB, bA are substantially equal (e.g., deviating by less than 5% or by less than 2%). If this is the case, it can be assumed that no background shift has taken place. If this is the case, on the other hand, it can be assumed that a background shift has taken place.

In other examples, it can be checked if the first and second axis intercepts bB, bA meet a predefined criterion. For example, it can be assumed that the first and second axis intercepts bB, bA have a predetermined relationship (e.g., it can be assumed that the first background parameter can be twice as large as the second background parameter based on the measurement setup). Then, it can be checked if the determined values for the first and second axis intercepts bB, bA follow this assumed relationship. If this is the case (e.g., a relationship between the first and second axis intercepts bB, bA deviates from an assumed relationship by less than a predetermined value), it can be assumed that no additional background shift has taken place. If this is the case, on the other hand, it can be assumed that an additional background shift has taken place.

In summary, the technique of the present disclosure may involve using a dynamic change in a measurement signal to determine if a background shift has happened at a predetermined point in time. In one example, the dynamic changing values can be analyzed by a linear regression technique to determine a relation between the measurement values in the first and second channels. This knowledge can then be used to extract a background signal for the group of measurements showing the change as well as for a group of measurements with substantially stationary measurement values. A comparison of the two background signals can allow an assessment if a background signal change has taken place or not.

In this manner, by using the techniques of the present disclosure, a background shift can be detected. Naturally, the background shift detection technique may not be 100% reliable in some examples. It may be the case that other factors can lead to a situation where the first and second axis intercepts bB, bA differ by more than a predetermined amount or do not fulfill a certain criterion even though no actual background shift has taken place.

Once a determination that a background shift has taken place has been made based on the first and second axis intercepts bB, bA, this information can be used in different ways in the analyzer. Aspects of these operations will be discussed next.

In one example, a warning message may be generated in response to detecting that a background shift has taken place. This warning message can be output to a user on a user interface (e.g., of the analyzer itself or of another device networked with the analyzer). In response to the warning, a user may decide what to do (e.g., to stop the analysis process and to resolve the issue having caused the background shift).

In addition or alternatively, the warning message may be internally processed in the analyzer. For instance, the automated analyzer can perform one or more predetermined actions to resolve the issue having caused the background shift. For instance, the analyzer can be configured to perform one or more of the steps including repositioning a sample container, cleaning a sample container, replacing a sample container, switching to a different measurement channel of the analyzer or recalibrating a measurement channel of the analyzer.

In addition or alternatively, information regarding a background shift can be added to a measurement data set to inform a user that these measurements likely include a background shift. Depending on the way how the measurements are used and processed, this information can be taken into account at a later point in time when evaluating the measurement data.

In still other examples, the automated analyzer may discard the measurements subject to a background shift and re-run the measurement. For example, the analyzer may use a new sample and/or a new sample container and re-run the measurement. Moreover, as discussed above, the analyzer may automatically identify the cause of the background shift, deal with the cause of the background shift and re-run the measurement.

In addition or alternatively to generating a warning message, the analyzer can be configured to correct the measurement data after having detected that a background shift has taken place. This process will be discussed in more detail in the subsequent passages.

In one example, a background shift can be quantified based on the first and second axis intercepts bB, bA and the slope m (e.g., or any other parameter indicating the relation between the measurements in the first and second channels). In some examples, a wavelength dependent background shift can be determined (i.e., a background shift which may have a different value for measurements at the first and second wavelengths $\lambda_1$, $\lambda_2$ in the first and second measurement channels). For instance, in a situation where a front surface of a sample vessel is titled compared to a light path of a measurement device as the result of a manipulation operation of the sample container, a wavelength dependent background shift can be expected. In other examples, a contamination of the sample container or the measurement device may result in a wavelength dependent background shift.

In other examples, a wavelength dependent background shift can be determined based on first and second axis intercepts bB, bA, the slope m (e.g., or any other parameter indicating the relation between the measurements in the first and second channels) and an assumed ratio between background shifts in the two wavelength channels (denoted as 'f' in the present disclosure).

The assumed ratio can be determined based on prior knowledge about the ratio of the background shifts in the two channels (e.g., at the two wavelengths $\lambda_1$, $\lambda_2$). In one example, the assumed ratio between the two background shifts can be 1 (i.e., the same background shift is assumed in both channels). In other examples, the assumed ratio between the two background shifts can be larger or smaller than 1.

Thus, the wavelength dependent background shifts in the first channel $\Delta b_1$ and in the second channel $\Delta b_2$ can be calculated as:

$$\Delta b_1 = (bA - bB)/(f - m), \text{ and} \qquad \text{(equation 2)}$$

$$\Delta b_2 = (bA - bB)/(1 - m/f). \qquad \text{(equation 3)}$$

Regardless of the technique used to quantify a background shift, the measurement data can be corrected by using the quantified background shift in some examples. For instance, in the example of FIG. 1, a background shift (which may be wavelength dependent or not) can be subtracted from the measurements in the second group ("group B"). In the example above, the measurements in the first channel of the second group ("group A") can be corrected by the first background shift $\Delta b_1$ (e.g., by subtracting the background shift from each measurement value) and the measurements in the second channel of the second group ("group A") can be corrected by the first background shift $\Delta b_2$ (e.g., by subtracting the background shift from each measurement value).

In this manner, a precision of the measurement data can be improved in some examples. In particular, deficiencies of bi-chromatic correction techniques in dealing with wavelength depending background shifts can be addressed in some examples.

In some examples discussed above, the background shift estimation and correction methods can take place during run-time of the analyzer. However, in other examples the techniques of the present disclosure can also be performed later in time on the measurement data (unless they necessarily have to be performed during runtime of the analyzer, e.g., when an operation of the analyzer is changed in response to the background shift estimation). In one example, the background shift estimation and correction methods can take place at a data processing device processing the measurement data taken by the analyzer.

After different aspects of the background shift estimation and correction techniques of the present disclosure have been discussed in connection with FIG. 1 to FIG. 3, automated analyzers having a background shift detection module can be discussed next in connection with FIG. 4 and FIG. 5.

In general, the background shift detection module can be configured to carry out any of the background shift estimation, determination, and correction techniques of the present disclosure. In some examples, the background shift detection module can be a local module at the analyzer. In other examples, the background shift detection module can be coupled to the analyzer through a network. In these examples, the background shift detection module can be part of another device or even distributed over different devices. Accordingly, the background shift detection module may not have to be a dedicated device configured to carry out the background shift determination and correction techniques of the present disclosure. Rather, the tasks of background shift detection module can be performed by any suitable computing system (e.g., a controller of an automated analyzer or a computer system networked with the automated analyzer).

Figure 4:
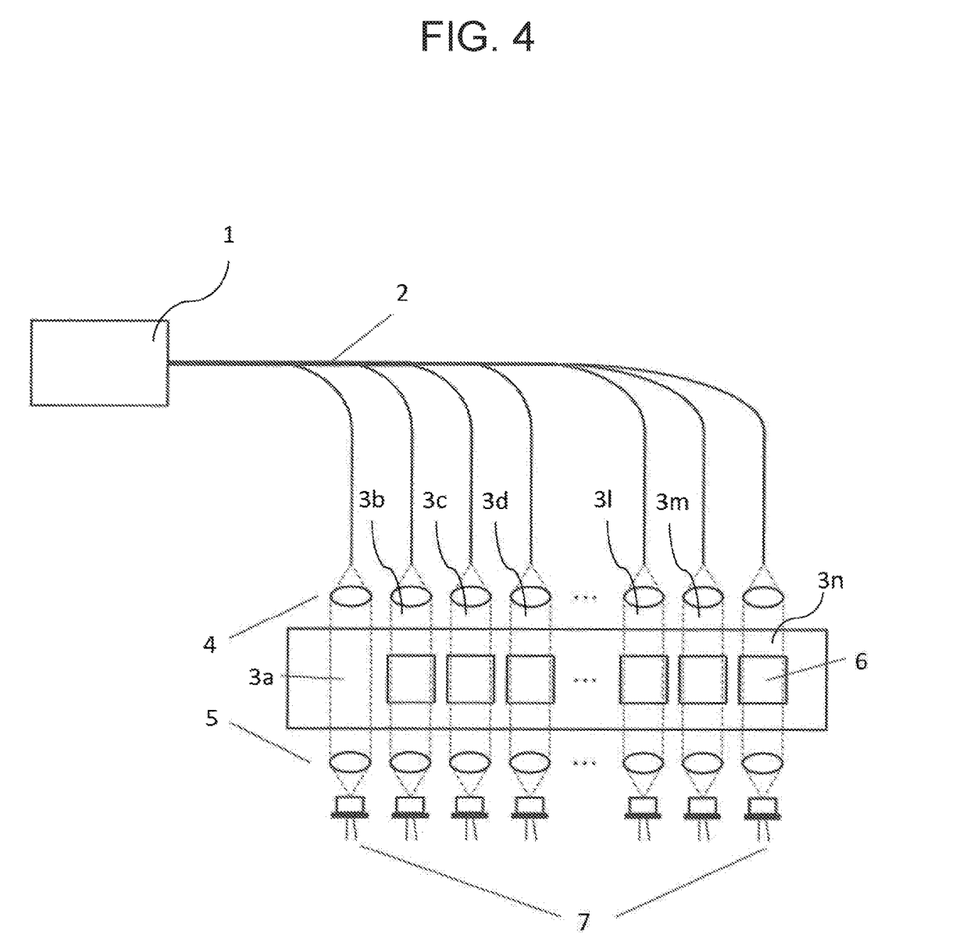
FIGS. 4-6 illustrate example analyzers according to an embodiment of the present disclosure.
Figure 5:
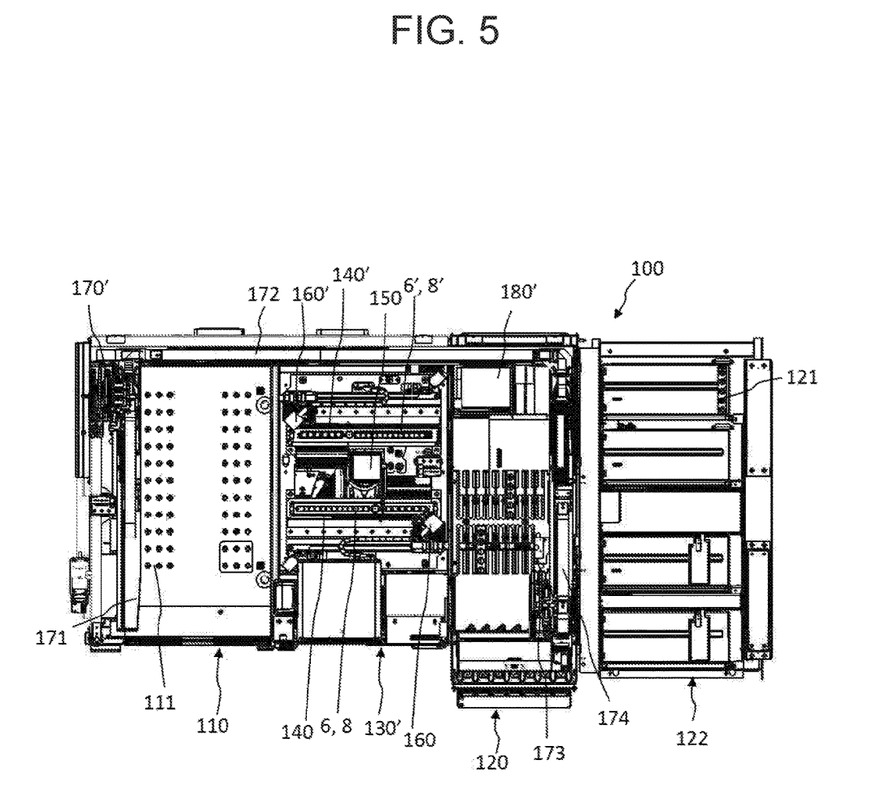
Figure 6:
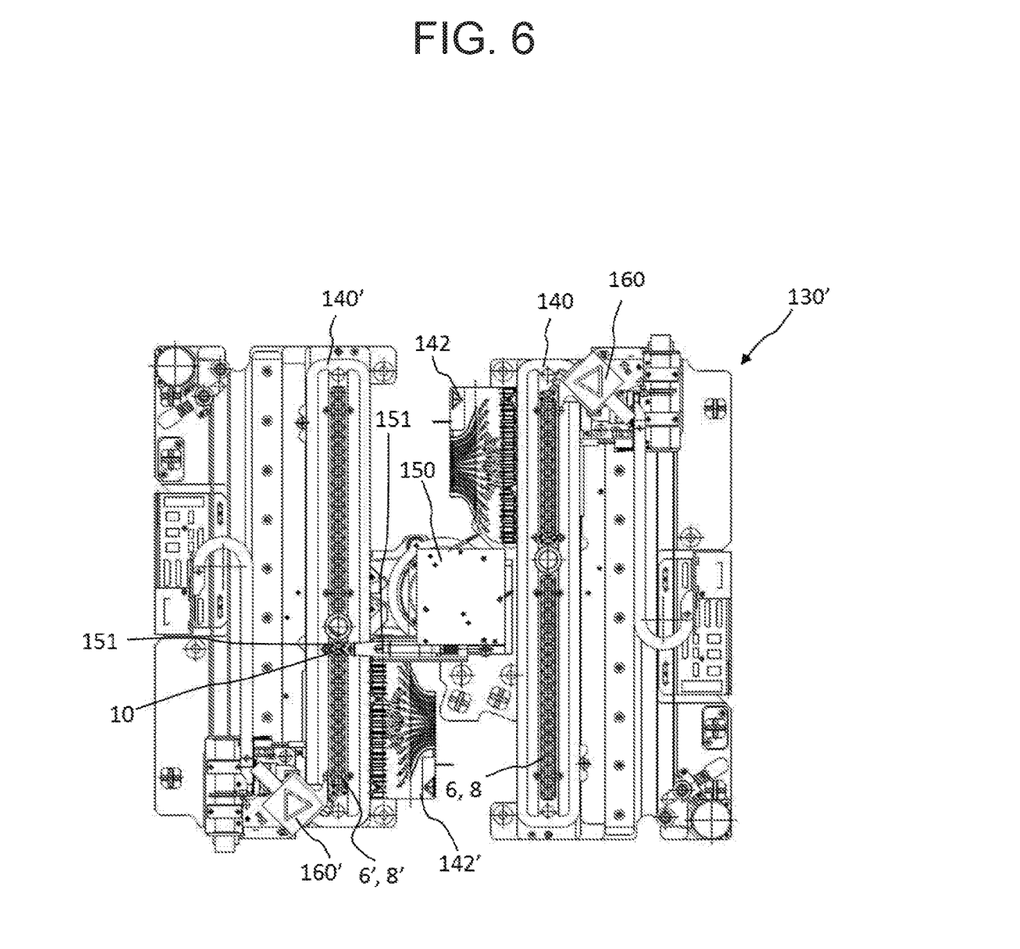

Having said that, FIG. 4 to FIG. 6 illustrate an example automated analyzer with a background shift detection module.

FIG. 4 shows a schematic drawing of an optical measurement device for samples including a plurality of measurement positions 3a, . . . 3n, a detector 7 configured to receive signals from the plurality of measurement positions 3a, . . . 3n and a controller (not shown in FIG. 1) configured to process the measurement data of the different measurement positions 3a, . . . 3n and to perform any one of the background shift detection, determination and/or correction techniques of the present disclosure. Thus, the controller of the analyzer can operate as background shift detection module.

In FIG. 4, each measurement position 3a, . . . 3n can include a respective optical fiber 2 for guiding light from light source 1 of the optical measurement device to a sample container 6 of a biological sample to be analyzed in the respective measurement channel. In addition, the detector 7 can include a plurality dedicated detectors, one for each measurement position 3a, . . . 3n. Moreover, each measurement position 3a, . . . 3n can be equipped with first optics adapted to guide light exciting a respective fiber 2 of the measurement position 3a, . . . 3n towards the respective measurement area. Furthermore, each optical measurement position 3a, . . . 3n can include second optics adapted to collect light emanating from the respective measurement area of the measurement channel and guide the collected light towards the respective detector 7. As can be seen in FIG. 4, the measurement position 3a, . . . 3n can operate in transmission (e.g., the measurement position 3a, . . . 3n can be arranged and configured so that light can pass through a sample contained in a sample container 6 arranged in the respective measurement position 3a, . . . 3n). The analyzer can be configured so that at each measurement position 3b, . . . 3n (or at least at a subset of these positions) measurements in the first and second channel can take place (e.g., at different wavelengths). In other examples, measurements in the first and second channels may take place at different measurement positions 3b, . . . 3n.

In FIG. 4, a particular setup of the optical measurement device is illustrated which has been discussed in the preceding sections. In one example, the optical measurement device can be a photometer which operates in transmission.

FIG. 5 and FIG. 6 show different views of an example of a system 100 for in-vitro diagnostic analysis (which can be a coagulation analyzer in some examples). The system 100 can comprise a reagent holding unit 110 for holding reagents to perform different coagulation tests. The reagent unit 110 can be embodied as a closed and tempered storage compartment, comprising access holes 111 for a pipetting nozzle to enter the compartment and withdraw an aliquot of reagent. The system 100 can further comprise a sample rack tray unit 122, which can be functionally coupled as a module to the sample loading/unloading unit 120 for loading/unloading sample racks 121 into/from the sample loading/unloading unit 120. The system can further comprise a central vessel processing area 130'. The vessel processing area 130' can comprise a first linear static vessel holder 140 and a second linear static vessel holder 140', the static vessel holders 140, 140' each comprising a plurality of vessel placement positions 6, 8, 6', 8' for holding vessels including biological samples (e.g., while the biological samples are incubated, or while optical measurements are performed on the biological samples). The vessel processing area 130' can further comprise a vessel input station 150 for feeding a vessel at a time to the static vessel holder 140. The vessel processing area 130' can further comprise first and second movable vessel workstations 160, 161' linearly translatable with respect to the respective static vessel holder 140, 140' and functionally coupled to the respective static vessel holder 140, 140' to transfer vessels between vessel placement positions 6, 8 of the static vessel holder 140.

The system 100 can further comprise two pipette heads (not shown in FIG. 5 or FIG. 6) translatably mounted on two respective horizontal arms comprising a plurality of pipetting devices each. The system 100 can further comprise a controller programmed to control the execution of a number of scheduled process operations including operation of the movable vessel workstations, of the pipette heads and of the pipetting devices.

It can be seen that during manipulation of the vessels in the automated analyzer different events that lead to a background shift discussed herein may occur. For instance, a vessel may not properly be placed in one of the plurality of vessel placement positions 6, 8, 6', 8' after having been moved to incubation station. In this situation, a controller of the automated analyzer can detect that a background shift has taken place (and, in some examples, correct the measurements based on a quantified estimated background shift as discussed in the present disclosure).

A method for determining a background shift comprised in optical measurement signals of an analyzer for samples is presented. The method can comprise obtaining a plurality of sets of optical measurements of a sample taken by the analyzer for samples at different points in time. Each set can include at least one measurement taken in a first channel and another measurement taken in a second channel different from the first channel. The plurality of sets of optical measurements can include one group of sets (A) and another group of sets (B). The measurements in the one group of sets (A) can be taken during a different period of time than the measurements in the other group of sets (B). The measurements in the one group of sets (A) can show a higher signal change than the measurements in the other group (B). The method can also comprise determining a first background signal based on a relation of measurements in the first and second channels in the one group (A), determining a second background signal based on a relation of measurements in the first and second channels in the one group (A) and the other group (B), and determining a background shift based on the first and second background signals.

The method can further comprise correcting measurements in the one or the other group (A, B) based on the determined background shift.

The method can further comprise determining if the background shift exceeds a threshold value and correcting measurements in the one or the other group (A, B) only if the calculated background shift exceeds the threshold value.

The method can further comprise providing an output indicating the determined background shift.

The method can further comprise determining if the background shift exceeds a threshold value and providing the output signal indicating the determined background shift only if the calculated background shift exceeds the threshold value.

The threshold can be an absolute threshold or a relative threshold determined based on a signal level of one or more measurements in the first or second channels.

The determination of a second background signal can include using a proportionality factor between measurements in the first and second channels determined based on measurements in the one group (A).

The determination of a first background signal based on a relation of measurements can include calculating an intercept and a slope of a relation between the measurements in the first and second channels of the one group (A). The determination of a first background signal based on a relation of measurements can include determining a correlation between the measurements in the first and second channels of the one group (A). The correlation can be a linear correlation.

The determination of a second background signal based on a relation of measurements in the first and second channels in the one group (A) and the other group (B) can include using a ratio of the measurements in the first and second channels. The determination of the second background signal can include averaging measurements in the first channel of the other group (B) or averaging measurements in the second channel of the other group (B).

The determination of the second background signal can include combining the measurements in the first channel of the other group (B) and the measurements in the second channel of the other group (B). One of the measurements in the first or second channel can be adjusted based on the first background signal. The measurements in the other group of sets (B) can be stationary.

The method can further comprise splitting the plurality of sets of optical measurements into the one and the other group of sets (A, B) based on identifying that a predetermined event takes place between the last set of measurements in the one and the other group of sets (A, B).

The predetermined event can include adding of a reagent to the sample being measured. The predetermined event can include one or more of a manipulation or movement of the sample. A manipulation or movement of a receptacle can include the sample, an adaptation of the measurement device performing the optical measurements, an adding of a reagent to the sample, or a change in the ambient conditions.

The method can further comprise splitting the plurality of sets of optical measurements into the one and the other group of sets (A, B) based on identifying that the sets of measurements in the one and the other group of sets (A, B) have at least one differing characteristic.

The measurements in the first and the second channels include measurement channels at different wavelengths. Center wavelengths of the first and the second channels can be spaced apart by less than 50 nm.

A computer readable medium having instructions thereon which, when executed by a controller of an analyzer, prompt the analyzer to carry out the operations of the above methods.

An automated sample analyze can comprise an optical measurement device configured to determine one or more parameters of a sample, the optical measurement device being configured to measure the parameter at least at a first channel and a second channel different from the first channel, and a background shift detection module configured to prompt the analyzer to carry out the operations of the above methods.

The background shift detection module can reside remote from the optical measurement device.

The background shift estimation detection can reside on one or more remote computer devices networked with the optical measurement device.

The optical measurement device can be configured to determine an absorption, a reflectance and/or a transmittance of a sample. The optical measurement device can include a photometer.

The analyzer can be a clinical chemistry analyzer, a coagulation chemistry analyzer, an immunochemistry analyzer, a urine analyzer, a hematology analyzer or a nucleic acid analyzer.

Further disclosed and proposed is a computer program including computer-executable instructions for performing the method according to the present disclosure in one or more of the embodiments enclosed herein when the program is executed on a computer or computer network. Specifically, the computer program may be stored on a computer-readable data carrier. Thus, specifically, one, more than one or even all of method steps as disclosed herein may be performed by using a computer or a computer network, preferably by using a computer program.

Further disclosed and proposed is a computer program product having program code, in order to perform the method according to the present disclosure in one or more of the embodiments enclosed herein when the program is executed on a computer or computer network. Specifically, the program code may be stored on a computer-readable data carrier.

Further disclosed and proposed is a data carrier having a data structure stored thereon, which, after loading into a computer or computer network, such as into a working memory or main memory of the computer or computer network, may execute the method according to one or more of the embodiments disclosed herein.

Further disclosed and proposed is a computer program product with program code stored on a machine-readable carrier, in order to perform the method according to one or more of the embodiments disclosed herein, when the program is executed on a computer or computer network. As used herein, a computer program product can refer to the program as a tradable product. The product may generally exist in an arbitrary format, such as in a paper format, or on a computer-readable data carrier. Specifically, the computer program product may be distributed over a data network.

Further disclosed and proposed is a modulated data signal which can contain instructions readable by a computer system or computer network, for performing the method according to one or more of the embodiments disclosed herein.

Referring to the computer-implemented aspects of the present disclosure, one or more of the method steps or even all of the method steps of the method according to one or more of the embodiments disclosed herein may be performed by using a computer or computer network. Thus, generally, any of the method steps including provision and/or manipulation of data may be performed by using a computer or computer network. Generally, these method steps may include any of the method steps, typically except for method steps requiring manual work, such as providing the samples and/or certain aspects of performing measurements.

Further disclosed and proposed is a computer, or computer network, comprising at least one processor. The processor can be adapted to perform the method according to one of the embodiments described in this description.

Further disclosed and proposed is a computer loadable data structure that can be adapted to perform the method according to one of the embodiments described in this description while the data structure is being executed on a computer.

Further disclosed and proposed is a storage medium. A data structure can be stored on the storage medium. The data structure can be adapted to perform the method according to one of the embodiments described in this description after having been loaded into a main and/or working storage of a computer or of a computer network.

It is noted that terms like "preferably," "commonly," and "typically" are not utilized herein to limit the scope of the claimed embodiments or to imply that certain features are critical, essential, or even important to the structure or function of the claimed embodiments. Rather, these terms are merely intended to highlight alternative or additional features that may or may not be utilized in a particular embodiment of the present disclosure.

Having described the present disclosure in detail and by reference to specific embodiments thereof, it will be apparent that modifications and variations are possible without departing from the scope of the disclosure defined in the appended claims. More specifically, although some aspects of the present disclosure are identified herein as preferred or particularly advantageous, it is contemplated that the present disclosure is not necessarily limited to these preferred aspects of the disclosure.

I claim:

1. A method for determining a background shift comprised in optical measurement signals of an analyzer for samples, the method comprising:

obtaining a plurality of sets of optical measurements of a sample taken by the analyzer at different points in time, wherein each set includes at least one measurement taken in a first channel ($l_1$) and another measurement taken in a second channel ($l_2$) different from the first channel;

dividing the plurality of sets of optical measurements into one group of sets (group A) and another group of sets (group B), wherein the measurements in the one group of sets (group A) are taken during a different period of time than the measurements in the other group of sets (group B) and wherein the measurements in the one group of sets (group A) show a larger signal change when compared to the measurements in the other group (group B);

determining a first background signal (bA) based on a relation of measurements in the first and second channels ($l_1$, $l_2$) in the one group (A) by determining a linear correlation between the measurements in the first and second channels ($l_1$, $l_2$) of the one group (A) and calculating an intercept (bA) and a slope (m) between the measurements in the first and second channels ($l_1$, $l_2$) of the one group (group A), wherein the first background signal corresponds to the intercept (bA);

determining a second background signal (bB) based on a relation of measurements in the first and second channels in the other group (B) by multiplying the measurements in the other group (B) taken in the first channel ($l_1$) by the slope (m) and subtracting measurements in the other group (B) taken in the second channel ($l_2$); and determining a background shift based on whether the first and second background signals (bA, bB) deviate by more than a threshold value.

2. The method of claim 1, further comprising:

correcting measurements in the one or the other group (group A, group B) based on the determined background shift.

3. The method of claim 2, further comprising:

correcting measurements in the one or the other group (group A, group B) only if the background shift exceeds the threshold value.

4. The method of claim 3, wherein the threshold value is an absolute threshold value or a relative threshold value based on a signal level of one or more measurements in the first or second channels ($i_1$, $l_2$).

5. The method of claim 1, further comprising:

providing an output indicating the determined background shift.

6. The method of claim 1, wherein determining the second background signal (bB) further includes averaging measurements in the first channel ($l_1$) of the other group (group B) or averaging measurements in the second channel (12) of the other group (group B).

7. The method of claim 1, wherein the measurements in the other group of sets (group B) are stable signal levels.

8. The method of claim 1, further comprising:

splitting the plurality of sets of optical measurements into the one and the other group of sets (group A, group B) based on identifying that a predetermined event takes place between a last set of measurements in the one group of sets (group A) and a first set of measurements in the other group of sets (group B), optionally wherein the predetermined event includes adding of a reagent to the sample being measured, manipulation or movement of the sample, a manipulation or movement of a receptacle including the sample, an adaptation of a measurement device performing the optical measurements, or a change in ambient conditions.

9. The method of claim 1, wherein measurements in the first and the second channels ($l_1$, $l_2$) include measurements at different wavelengths.

10. A computer readable medium having instructions thereon which, when executed by a controller of an analyzer, prompt the analyzer to carry out the method of claim 1.

11. An automated sample analyzer, the automated sample analyzer comprising:

an optical measurement device configured to determine one or more parameters of a sample, the optical measurement device being configured to measure the one or more parameters at least at a first channel and a second channel different from the first channel; and a background shift detection module configured to prompt the analyzer to carry out the method of claim 1.

* * * * *